United States Patent [19]

della Valle et al.

[11] Patent Number: 5,045,532
[45] Date of Patent: Sep. 3, 1991

[54] INNER ESTERS OF GANGLIOSIDES WITH ANALGESIC-ANTIINFLAMMATORY ACTIVITY

[75] Inventors: Francesco della Valle, Padua; Aurelio Romeo, Rome, both of Italy

[73] Assignee: Fidia, S.p.A., Abano Terme, Italy

[21] Appl. No.: 260,067

[22] Filed: Oct. 20, 1988

[30] Foreign Application Priority Data

Nov. 2, 1987 [IT] Italy .............................. 48565 A/87

[51] Int. Cl.$^5$ .............................................. A61K 31/70
[52] U.S. Cl. ......................................... 514/25; 514/23; 514/61; 514/62; 536/4.1; 536/53; 536/55.1; 536/20
[58] Field of Search .................... 536/53, 1.1, 55.1, 20, 536/4.1; 514/25, 26, 28, 23, 61, 62

[56] References Cited

U.S. PATENT DOCUMENTS

| | | | |
|---|---|---|---|
| 4,476,119 | 10/1984 | della Valle et al. | 514/25 |
| 4,593,091 | 6/1986 | della Valle et al. | 536/55.1 |
| 4,639,437 | 1/1987 | della Valle et al. | 514/54 |
| 4,707,469 | 11/1987 | della Valle et al. | 514/26 |
| 4,716,223 | 12/1987 | della Valle et al. | 536/20 |

FOREIGN PATENT DOCUMENTS 0145209 6/1985 European Pat. Off. .
0167449 1/1986 European Pat. Off. .

OTHER PUBLICATIONS

Chemical Abstracts, vol. 102, No. 9, No. 72705f (4 Mar. 1985).
Chemical Abstracts, vol. 96, No. 23, No. 193351d (7 Jun. 1982).
Archives internationales de Pharmacodynamie et de Therapie, vol. 272, No. 1, Nov. 1984, M. Amico-Roxas et al. (full text copy of above Chem. Abstracts 193351d).
Riboni et al.; J. Biol. Chem., 261(18):8514-8519 (1986).
Gorio et al.; Brain Research, 197:236-241 (1980).
Samson; Drugs of Today, 22(2):73-107 (1986).

*Primary Examiner*—Donald W. Griffin
*Assistant Examiner*—Nancy S. Carson
*Attorney, Agent, or Firm*—Birch, Stewart, Kolasch & Birch

[57] ABSTRACT

A pharmaceutical composition is provided comprising inner ester ganglioside derivatives useful for its peripheral analgesic-antiinflammatory activity in treating pain caused by pathologies of the peripheral nervous system and which can advantageously be administered orally.

20 Claims, No Drawings

INNER ESTERS OF GANGLIOSIDES WITH ANALGESIC-ANTIINFLAMMATORY ACTIVITY

BACKGROUND AND FIELD OF THE INVENTION

The present invention concerns a new therapeutic application of the inner ester derivatives of gangliosides.

U.S. Pat. No. 4,476,119 and European Pat. No. 0072722 describe the preparation of the inner ester gangliosides and the use of the compounds as being valuable agents in the treatment of pathologies affecting the nervous system after trauma or diseases which in some way damage the nervous tissue, and as being more efficacious than gangliosides themselves.

The present invention reports the significant analgesic-antiinflammatory activity of individual inner ester gangliosides, in particular the inner ester of $GM_1$, and of a mixture of inner ester gangliosides.

Gangliosides are a group of glycosphingolipids with a structure containing one saccharide part bound to a ceramide and to a sialic group. The saccharide part is composed of at least one galactose or glucose and of at least one N-acetylglucosamine or N-acetylgalactosamine.

The general structure of a ganglioside may therefore be represented by the following formula:

| one mole of sialic acid | one mole of ceramide at least one mole of galactose or glucose at least one mole of N-acetylglucosamine or N-acetylgalactosamine |
| --- | --- | in which these compounds are bound by glucosidic bonds.

Numerous gangliosides have been identified which have proved to be particularly abundant in the nervous tissue, especially in that of the brain. Various studies have demonstrated that the sialic groups most frequently encountered in gangliosides are N-acetylneuraminic acid (NANA) and to a lesser extent, N-glycolylneuraminic acid. Of the numerous gangliosides identified, the following gangliosides, classified by their international symbols, were found to exist in considerable measure in the mixtures derived from bovine brain tissue:

$GD_{1b}$ (16%)

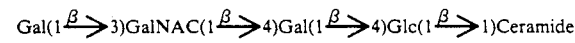

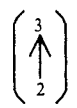

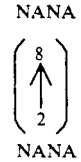

$GT_{1b}$ (19%)

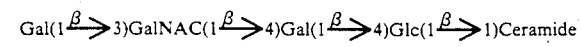

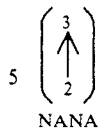

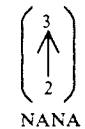

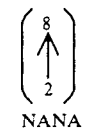

$GM_1$ (21%)

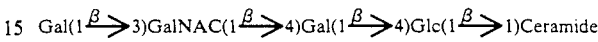

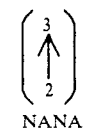

$GD_{1a}$ (40%)

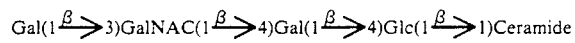

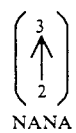 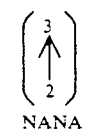

where Glc stands for glucose, GalNAC stands for N-acetylgalactosamine, Gal stands for galactose, NANA stands for N-acetylneuraminic acid and the percentages in parenthesis indicate the quantity of each ganglioside found in a mixture of gangliosides extracted from bovine brain tissue.

It is well known that gangliosides play an important role in the nervous system and it has recently been shown that gangliosides are useful in therapy for pathologies of the peripheral and central nervous systems [Acta Psychiat. Scand., 55, 102, (1977); Brain Res. 197, 236, (1980); Drugs of Today 22, 73–107, (1986)].

The therapeutic action of gangliosides seems to consist above all in stimulating sprouting phenomena of the nerve cell and in activating the membrane enzymes implicated in the conduction of nervous stimuli, such as for example the enzyme $(Na^+,K^+)ATPase$ [Brain Res., 197, 236, (1980), J. of Neurochem. (1981)].

Neuronal sprouting stimulated by gangliosides enhances functional recovery of the damaged nervous tissue.

Subsequent studies have shown that inner ester gangliosides are more efficacious than starting gangliosides in the therapy of nervous system pathologies. See for example the above-noted U.S. Pat. No. 4,476,119.

It is also known that gangliosides have a specific and strong antinociceptive activity, that is, they are efficacious in reducing writhings induced by phenylquinone and acetic acid and the increase in permeability induced by acetic acid [Arch. Int. Pharmacodyn. 272, 103–117 (1984)].

DETAILED DESCRIPTION OF THE INVENTION

It has now been determined according to the present invention that inner ester gangliosides possess analgesic-antiinflammatory activity and that the analgesic-antiinflammatory efficacy of the inner ester gangliosides is greater than that shown by starting gangliosides. These studies have also revealed the considerable advantage that such inner esters can be administered by oral route for the treatment of pain and inflammation.

Only some of the possible inner ester derivatives of gangliosides have been isolated from the nervous tissue where they are present only in very small quantities [J. Biol. Chem. 261, 8514–19 (1986); Glycoconiugate J. 4, 19-127 (1987)].

The inner ester derivatives of gangliosides are produced from the reaction between the carboxy group of a sialic acid with the hydroxy group of one of the saccharide units or of another adjacent sialic acid in the same ganglioside molecule [J. of Neurochemistry, 34, 1351, (1980), Bull of Molecular Biology and Medicine 3, 170, (1978)]. As an example, the following is the structure of one inner ester of a ganglioside:

group of one of the saccharide units, specifically galactose. The formation of the inner ester bond, together with the normal glucosidic bond between the sialic acid and carbohydrate moiety, creates a lactonic ring, typically five or six-membered, characteristic of the structure of the inner ester ganglioside derivatives. While Formula I has been shown for exemplary purposes, it is to be noted that other lactonic rings having 5 or more membered ring structures could be formed as the sialic acid carboxyl group ester bonds with the hydroxyl group of a carbohydrate moiety.

As noted above, the inner ester derivatives of gangliosides may also be formed when the carboxy group of a sialic acid is esterified by a hydroxy group of another sialic acid bound to the first by means of a glucose bond in the gangliosides molecule.

This structure can be represented by the following

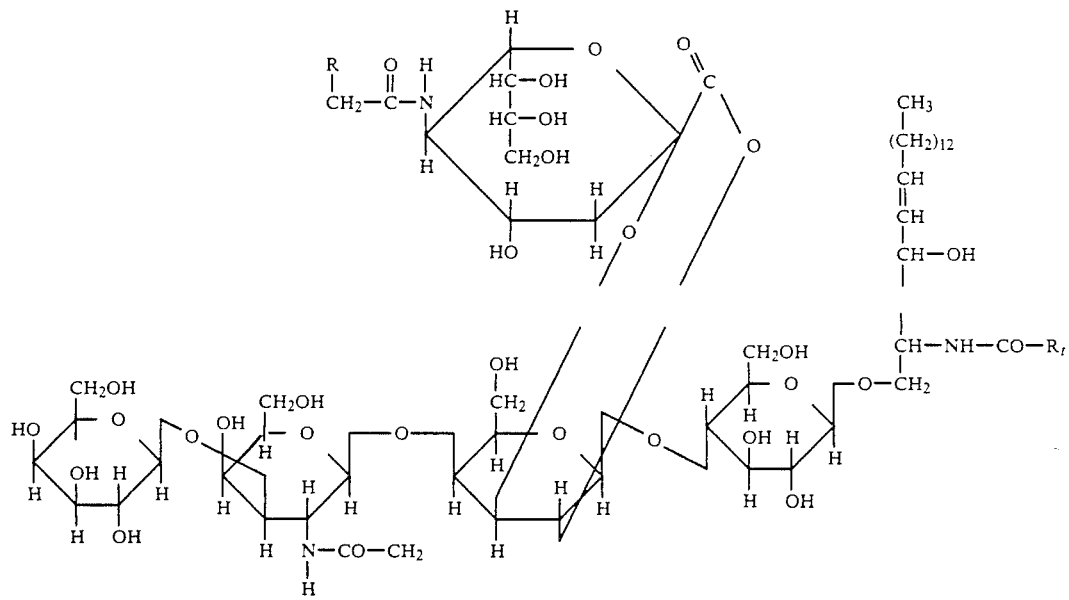

where R in the sialic acid is H or OH and $R_1$ in the ceramide group is a fatty acid residue such as oleic, stearic or linoleic acid. The inner ester ganglioside derivative (I) is a derivative in which the carboxy group of the sialic acid is bound by esterification to a hydroxy formula:

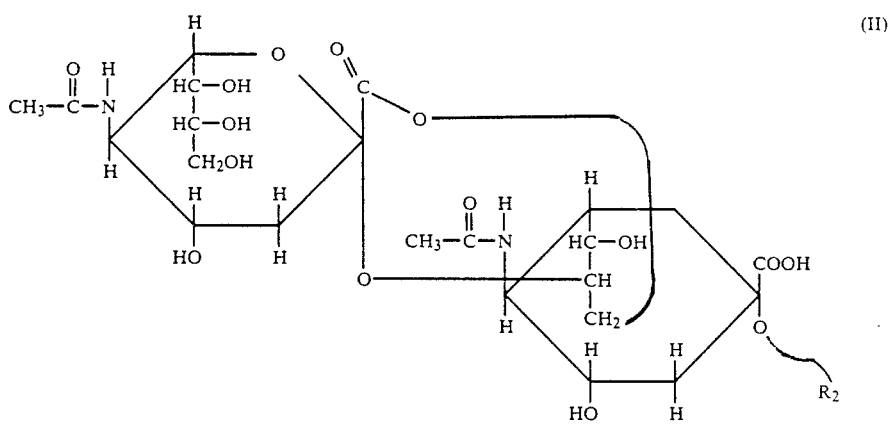

where $R_2$ represents the saccharide part bound by means of a glucoside bond to sialic acid. Another possible inner ester derivative of gangliosides can be represented by the following formula:

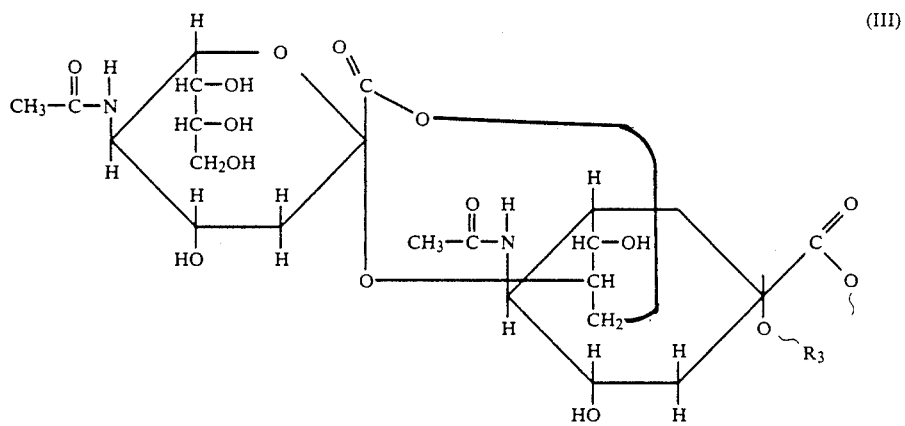

(III)

where R₃ represents the saccharide part to which the adjacent sialic acid is bound by esterification. In this case formula (III) represents an inner ester ganglioside derivative in which a sialic acid is bound by esterification to an adjacent part. Clearly, therefore, it is possible to obtain many variations of the derivatives described in such a way that the inner ester derivatives of gangliosides are generally formed by a saccharide part, at least one ceramide and at least one sialic acid in which one or more sialic acids are bound by esterification to a saccharide unit and/or one or more sialic acids are bound by esterification to an adjacent sialic acid. Numerous inner ester derivatives of gangliosides are therefore possible of which those described previously are merely an example.

A new and improved method for the preparation of inner ester ganglioside derivatives, allowing high yields of such derivatives, is described in the present applicant's prior U.S. Pat. No. 4,593,091 and European Pat. 0072722. This method includes the reaction of gangliosides with a lactonizing reagent in a non-aqueous organic solvent in anhydrous conditions. The parent ganglioside compounds used for preparation of the inner ester derivatives can be prepared according to per se known methods, and can be obtained as preparations of individual gangliosides or as a mixture of gangliosides. For example, the individual gangliosides can be those extracted from bovine brains such as described in the article "Gangliosides of the Nervous System" in Glycolipid Methodology, Lloyd A. Witting Fd., American Oil Chemists' Society, Champaign, Ill., 187–214 (1976) including gangliosides GM4, GM3, GM1, GD2, GD1a—GalNAC, $G_{T1c}$, $G_Q$, and $T_{T1}$. The individual ganglioside GM1 can be prepared for example, by the extraction and purification method of Tettamanti et al., Biochim. Biophys. Acta, 296:160–170 (1973).

If ganglioside mixtures are used as the starting material for preparation of a mixture of inner esters, the mixtures may consist of those directly obtained by extraction of gangliosides from various animal tissues as "total" ganglioside extracts or as various fractions thereof. Such extracts are described in literature for example, in the articles mentioned above or also in "Extraction and analysis of materials containing lipid-bound sialic acids" in Glycolipid Methodology, Lloyd A. Witting Fd., American Oil Chemists' Society, Champaign, Ill. 159–186 (1976) and "Gangliosides of the Nervous System" from the same book, pp. 187–214. Some of the most important mixtures to be used according to the present invention are ganglioside extracts obtained from tissues from the nervous system, in particular from the brain, and containing gangliosides $G_{M1}$, $G_{D1a}$, $G_{D1b}$ and $G_{T1b}$ already mentioned above. These mixtures preferably contain 19–23% by weight of $G_{M1}$, 36–44% by weight $GD_{1a}$, 14–18% by weight $GD_{1b}$ and 17–21% by weight $GT_{1b}$. Mixtures of this type are for example those described in Preparation Example A.

In the process for the preparation of the inner ester derivatives, the most suitable organic solvents for use according to the aforesaid inventions include dimethylsulfoxide (DMSO), dimethylformamide (DMF), sulfolane, tetrahydrofuran, dimethoxyethane, pyridine or mixtures of these solvents. Suitable reagents for lactonization include carbodiimides soluble in organic solvents such as dicyclohexylcarbodiimide, benzylisopropylcarbodiimide, benzylethylcarbodiimide, salts of 2-chloro-1-methylpyridine, ethoxyacetylene and the Woodward reagent (N-ethyl-5-phenylisoxazol-3'-sulfonate). While previous methods for the reaction of gangliosides with a carbodiimide in aqueous medium gave very low yields of inner ester derivatives, it has been found that by the procedure according to the aforesaid patents, performing the reaction of gangliosides in a non-aqueous medium, very high yields are obtained, that is, essentially quantitative yields of inner ester derivatives, in greater quantities than possible by previous methods. The starting gangliosides used in this procedure are extracted from mammal, preferably bovine, brain tissues.

Preparation Example A—Preparation of a ganglioside mixture

Bovine brain cortex, removed from the animal, is homogenized in phosphate buffer at pH 6.8; 6 volumes of tetrahydrofuran are added and the resulting mixture is centrifuged. The supernatant is re-extracted twice with tetrahydrofuran. After contrifugation the non-polar materials are removed by separation with ethyl ether and the aqueous-tetrahydrofuranic layer is introduced on an ionic exchange column balanced with 50% ethanol. Barium hydroxide and four volumes of ice cold ethanol are added to the effluent from the column.

After 18 hours in cold conditions, the precipitate is gathered and then slightly acidified with hydrochloric acid after solution in water. The solution thus obtained is dialyzed and freeze-dried. The yield at this point is of about 0.6 mg of raw ganglioside mixture per gram of nervous tissue used. The freeze-dried powder is dispersed in 20 volumes of chloroform-methanol 2:1, the solution obtained is filtered until it is perfectly clear, and then separated by adding 0.2 volumes of a solution of potassium chloride in water at 0.88%.

The upper layer is separated, dialyzed and freeze-dried. The final yield is of about 0.3 mg of purified mixture of ganglioside salts per gram of brain tissue.

EXAMPLE 1

A mixture of gangliosides is obtained by extraction from bovine brains, according to Preparation Example A, and 5g of this mixture are dissolved in 50 ml of DMSO. Then, 4g of anhydrous styrene type resin (sulfonic acid)(50-100 mesh, H+form) are added to the mixture and the resulting system is stirred for 30 minutes at room temperature. This treatment with an ion exchange resin converts all of the ganglioside carboxylate groups to —COOH (carboxyl) groups. Complete conversion of the carboxylate groups is confirmed by an appropriate physical analytical method, such as atomic absorption. The resin is then filtered under suction and the solution is treated with 1.5 g of dicyclohexylcarbodiimide and allowed to stand for one hour. The dicyclohexylurea which precipitates is removed by filtration and the remaining solution is treated with 100 ml of acetone causing precipitation of the product inner ester ganglioside derivatives. The method yields 4.6 g of inner ester product (about 90-95% of the theoretical value).

The presence of the inner ester derivatives is confirmed by infrared spectroscopy and by thin layer chromatography.

IR Spectroscopy - Performed on a KBr pellet, the esterlactone bond produces a band at 1750 cm$^{-1}$.

Thin Layer Chromatography - On silica gel plates, solvent system $CHCl_3/MeOH/0.3\%$ $CaCl_2$ (55:45:10, v/v/v), the $R_f$ of the mixture of internal esters ranges between 0.7 and 0.85. The $R_f$ of the final products exceeds the $R_f$ of the mixture of the starting compounds. The chromatography results thus show the absence of any starting material. By treatment with a 0.1N solution of $Na_2CO_3$ at 60° C. for 1 hour, the ester bonds are cleaved and the original mixture of starting ganglioside compounds can be obtained.

The ganglioside mixture obtained can be fractioned in various portions substantially representing pure gangliosides using silicic acid columns and eluting with a mixture of methanol-chloroform. In this way a composition of inner ester gangliosides is obtained of about 40% of the ganglioside $D_{D1a}$, 21% of the ganglioside $GM_1$, 19% of the ganglioside $G_{T1b}$ and 16% of the ganglioside $G_{D1b}$.

EXAMPLE 2

9 g of a ganglioside mixture (sodium salt) are dissolved in 80 ml of distilled water and passed through a column filled with 20 g of Dowex 50 w×b 8 (100-200 mesh triethylammonium form).

This product, anhydrified in high vacuum, is dissolved (with the aid of a sonicator bath) in 200 ml of anhydrous tetrahydrofuran containing 8 ml of triethylamine.

This solution is slowly added to 600 ml of anhydrous tetrahydrofuran (4 hours) containing 40 mM of 2-chloro-1-methyl-pyridinium salt (where the anion could be, for example, iodide, toluene-4-sulfonate, trifluoromethane sulfonate, etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 90 ml of chloroform/ethanol 1:1 and precipitated in 450 ml of acetone. The product is finally dried in high vacuum.

Yield - 7.9 g (89.7% of the theoretical value).

Thin layer chromatography: On silica gel plates, solvent system chloroform/methanol/$CaC_2$ 0.3%, 55:45:10, the $R_f$ of the mixture of inner esters ranges between 0.7 and 0.85. The $R_f$ of the final products exceeds the $R_f$ of the mixture of the starting compounds. The chromatography results thus show the absence of any starting material. By treatment with 0.1N solution of $Na_2CO_3$ at 60° C. for one hour, the ester bonds are cleaved and the original ganglioside compounds can be obtained.

The IR spectrum of the inner or internal esters of the ganglioside mixture, performed on a KBr pellet, shows the typical ester absorption of 1750 cm$^{-1}$.

EXAMPLE 3

8 g of $GM_1$ (sodium salt) are dissolved in 80 ml of distilled water and passed through a column filled with 10 g of Dowex 50 w×8 (100-200 mesh triethylammonium form).

This product, anhydrified in high vacuum, is dissolved (with the aid of a sonicator bath) in 200 ml of anhydrous tetrahydrofuran containing 4 ml of triethylamine.

This solution is slowly added to 600 ml of anhydrous tetrahydrofuran (4 hours) containing 20 mM of 2-chloro-1-methyl-pyridinium salt (where the anion could be, for example, iodide, toluene-4-sulfonate, trifluoromethane sulfonate etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 80 ml of chloroform/methanol 1:1 and precipitated in 400 ml of acetone. The product is finally dried in high vacuum.

Yield - 7.0 g (88.4% of the theoretical value).

Thin layer chromatography: On silica gel plates, solvent system chloroform/methanol/$CaCl_2$ 0.3%, 55:45:10, the $R_f$ of the final product (0.70) exceeds the $R_f$ (0.65) of the starting compound. The chromatography results thus show the absence of any starting material. By treatment with 0.1N solution of $Na_2CO_3$ at 60° C. for one hour, the ester bond is cleaved and the original ganglioside can be obtained.

The IR spectrum of the inner ester of $GM_1$, performed on a KBr pellet, shows the typical ester absorption of 1750 cm$^{-1}$.

EXAMPLE 4

9 g of a ganglioside mixture (sodium salt) are dissolved in 80 ml of distilled water and passed through a column filled with 20 g of Dowex 50 w×8 (100-200 mesh pyridinium form).

This product, anhydrified in high vacuum, is dissolved in 800 ml of anhydrous tetrahydrofuran and 4.2 g (60 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1:1 and precipitated in 400 ml of acetone.

Yield - 8.1 g (92.0% of the theoretical value).

Thin layer chromatography: On silica gel plates, solvent system chloroform/methanol/CaCl$_2$ 0.3%, 55:45:10, the R$_f$ of the mixture of inner ester ranges between 0.7 and 0.85. The R$_f$ of the final products exceeds the R$_f$ of the mixture of the starting compounds. The chromatography results thus show the absence of any starting material. By treatment with 0.1N solution of Na$_2$CO$_3$ at 60° C. for one hour, the ester bonds are cleaved and the original ganglioside compounds can be obtained.

The IR spectrum of the inner esters of the ganglioside mixture, performed on a KBr pellet, shows the typical ester absorption of 1750 cm$^{-1}$.

EXAMPLE 5

8 g of GM$_1$ (sodium salt) are dissolved in 80 ml of distilled water and passed through a column filled with 10 g of Dowex 50 w ×8 (100–200 mesh pyridinium form).

This product, anhydrified in high vacuum, is dissolved in 800 ml of anhydrous tetrahydrofuran and 2.1 g (30 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1:1 and precipitated in 400 ml of acetone.

Yield - 7.2 g (91.0% of the theoretical value).

Thin layer chromatography: On silica gel plates, solvent system chloroform/methanol/CaCl$_2$ 0.3%, 55:45:10, the R$_f$ of the final product (0.70) exceeds the R$_f$ (0.65) of the starting compound. The chromatography results thus show the absence of any starting material. By treatment with 0.1N solution of Na$_2$CO$_3$ at 60° C. for one hour, the ester bond is cleaved and the original ganglioside can be obtained.

The IR spectrum of the inner ester of GM$_1$ performed on a KBr pellet, shows the typical ester absorption of 1750 cm$^{-1}$.

EXAMPLE 6

9 g of ganglioside mixture (sodium salt) are dissolved in 80 ml of distilled water and passed through a column filled with 20 g of Dowex 50 w ×8 (100–200 mesh pyridinium form).

This product, anhydrified in high vacuum and dissolved in 200 ml of anhydrous pyridine, is added to a suspension of 5.52 g (10 mM) of the Zwitterionic Woodward reagent (N-ethyl-5-phenylisoxazolium-3'-sulfonate, Woodward et al., J. Am. Chem. Soc. 83, 1010–1012, 1961) in 200 ml of anhydrous pyridine. This reaction mixture is stirred for 10 days at room temperature.

After filtration of the excess reagent and complete removal of the solvent, the residue is dissolved in 90 ml of chloroform/methanol 1:1 and precipitated in 450 ml of acetone.

Yield - 7.2 g (81.8% of the theoretical value).

Thin layer chromatography: On silica gel plates, solvent system chloroform/methanol/CaCl$_2$ 0.3%, 55:45:10, the R$_f$ of the mixture of inner esters ranges between 0.7 and 0.85. The R$_f$ of the final products exceeds the R$_f$ of the mixture of the starting compounds. The chromatography results thus show the absence of any starting material, by treatment of 0.1N solution of Na$_2$CO$_3$ at 60° C. for one hour, the ester bonds are cleaved and the original ganglioside compounds can be obtained.

The IR spectrum of the inner esters of the ganglioside mixture, performed on a KBr pellet, shows the typical ester absorption of 1750 cm$^{-1}$.

EXAMPLE 7

8 g of GM$_1$ (sodium salt) are dissolved in 80 ml of distilled water and passed through a column filled with 10 g of Dowex 50 w×8 (100–200 mesh pyridinium form).

This product, anhydrified in high vacuum and dissolved in 200 ml of anhydrous pyridine, is added to a suspension of 1.26 g (5 mM) of the Zwitterionic Woodward reagent (N-ethyl-5-phenylisoxazolium-3'-sulfonate), in 200 ml of anhydrous pyridine. This reaction mixture is stirred for 10 days at room temperature.

After filtration of the excess reagent and complete removal of the solvent, the residue is dissolved in 80 ml of chloroform/methanol 1:1 and precipitated in 400 ml of acetone.

Yield -6.3 g (79.5% of the theoretical value).

Thin layer chromatography: On silica gel plates, solvent system chloroform/methanol/CaCl$_2$ 0.3%, 55:45:10, the R$_f$ of the final product (0.70) exceeds the R$_f$ (0.65) of the starting compound. The chromatography results thus show the absence of any starting material. By treatment with 0.1N solution of Na$_2$CO$_3$ at 60° C. for one hour, the ester bond is cleaved and the original ganglioside can be obtained.

The IR spectrum of the inner ester of GM$_1$ performed on a KBr pellet, shows the typical ester absorption of 1750 cm$^{-1}$.

PHARMACOLOGICAL PROPERTIES

The above noted patents, U.S. Pat. No. 4,476,119 and EP 0072722, describe inner ester derivatives of gangliosides, methods for producing such derivatives, their efficacy in the therapy of pathologies of the nervous system and their stronger activity as compared to that of gangliosides themselves. The inner ester derivatives of gangliosides may be used to treat a whole range of nervous diseases, including pathologies of the peripheral and central nervous systems which occur following disease or trauma. These substances may also be used in post-surgical therapy following operations involving motor and sensory nerves such as surgery for herniated disks.

On the basis of the present invention, the inner ester derivatives of gangliosides, and particularly the inner esters of GM$_1$, have been found to have specific and valuable analgesic-antiinflammatory properties (peripheral).

A previous publication [Arch. Int. Pharmacodyn. 272, 103–117 (1984)] has reported the antinociceptive properties of a ganglioside mixture, that is, the ability of the mixture to reduce, after subcutaneous administration, the number of writhings induced by phenylquinone (and by acetic acid) and to reduce the increase in permeability induced by acetic acid.

Antiinflammatory activity evaluated by the acetic acid-induced peritonitis test in rat Methods: The study was carried out on Sprague-Dawley male rats weighing 300–350 gr.

Evaluation was made of the capacity of gangliosides to inhibit the formation of peritoneal exudate following intraperitoneal injection (10 ml/kg) of a solution of 0.5% acetic acid. The products in examination, the inner ester of $GM_1$, the inner ester ganglioside mixture (GA inner esters) and the ganglioside mixture itself (GA) were administered by oral and subcutaneous routes (solubilized in 10 ml/kg of saline) 30 minutes before injection of acetic acid. The control animals received 10 ml/kg of saline. 30 minutes after induction of the exudate the animals were sacrificed, the exudate was extracted and the percentage of inhibition was calculated according to the control values.

Results of the acetic acid-induced peritonitis test

From the results summarized in Table 1, it is clear that the antiexudative activity of the inner ester of $GM_1$ and of the inner ester ganglioside mixture is greater than that of the GA mixture itself.

The two inner ester formulations begin to be effective at very low dosages, 1-2 mg/kg, and furthermore this activity is maintained after oral administration, unlike that of the GA mixture.

TABLE 1

Results of the acetic acid-induced peritonitis test in rat with intraperitoneal injection (10 ml/kg) of a solution of 0.5% acetic acid in (10 mg/kg)

|  | Dose mg/kg | No. of animals | % inhibition |
|---|---|---|---|
| s. c. treatment |  |  |  |
| controls (saline 10 ml/kg) | — | 40 | — |
| GA | 10 | 20 | 23.2 |
|  | 30 | 20 | 40.3 |
| $GM_1$ inner ester | 1 | 20 | 40.7 |
|  | 2 | 20 | 45.1 |
| GA inner ester | 1 | 20 | 34.2 |
|  | 2 | 20 | 39.8 |
| os treatment |  |  |  |
| controls (saline 10 ml/kg) | — | 40 | — |
| GA | 10 | 20 | 22.1 |
|  | 30 | 20 | 37.8 |
| $GM_1$ inner ester | 1 | 20 | 38.1 |
|  | 2. | 20 | 42.3 |
| GA inner ester | 1 | 20 | 35.0 |
|  | 2 | 20 | 40.5 |

The present invention relates to the improved analgesic-antiinflammatory properties of the inner ester gangliosides in mixture, of the individual inner ester gangliosides, and of, in particular, the inner ester derivative of $GM_1$ as compared to starting gangliosides. The efficacy of the inner esters when administered orally is also a part of the present invention. The pharmacological properties of the inner ester derivatives of gangliosides, and of the inner ester of $GM_1$, are better than those of gangliosides, as can be seen from the following tests conducted to show the improved and unexpectedly superior activity of the inner ester gangliosides:

Analgesic activity evaluated by the "writhing" test with phenylbenzoquinone in mouse Methods: The study was effected using male Swiss mice (26-28 gr). Evaluation was made of pain reaction induced by intraperitoneal injection of 0.25 ml/mouse of a solution of 0.02% phenylquinone in 5 gr of ethyl alcohol. This type of injection induces a pain reaction manifested by abdominal writhings of the animal.

The study evaluated the effect of the inner ester of $GM_1$, of the inner ester ganglioside mixture (GA inner ester) as well as of a ganglioside mixture itself (hereafter known by the abbreviation GA). The gangliosides in examination and the mixture were administered by subcutaneous (s.c. treatment) and oral routes (os treatment) (solubilized in 10 ml/kg of saline) 30 minutes before administration of phenylquinone.

The control animals received 10 ml/kg of saline. The number of writhings effected by each animal over an interval of 5 minutes was evaluated (from the 5th to the 10th minute after phenylquinone injection), and then the percentage of inhibition to nervous pain reaction was calculated, compared to controls.

Results of the writhing test

The results are summarized in Table 2.

From the presented data, it is easy to see the high degree of efficacy of the two esters, compared to the ganglioside mixture. From this comparison it can be seen that the two inner ester formulations are active at very low dosages (0.5-1 mg/kg), lower than the effective dose of the ganglioside mixture. In addition, the percentage of inhibition is very high (60-70%) for the inner esters, higher than that obtained by the GA mixture at the same dosages. Finally, the activity of the two inner ester formulations is reached and is comparable in the two administration routes, unlike the ganglioside mixture GA, which shows much lower activity when administered orally.

TABLE 2

Results of the writhing test in mouse with intraperitoneal injection (0.25 ml) of a 0.25% solution of phenylquinone in 5% ethyl alcohol

|  | Dose mg/kg | No. of animals | % inhibition |
|---|---|---|---|
| s.c. treatment |  |  |  |
| controls (saline 10 mg/kg) | — | 40 | — |
| GA | 1.0 | 20 | 40.0 |
|  | 2.5 | 20 | 55.1 |
| $GM_1$ inner ester | 0.5 | 20 | 49.1 |
|  | 1.0 | 20 | 69.5 |
| GA inner ester | 0.5 | 20 | 58.2 |
|  | 1.0 | 20 | 70.3 |
| os treatment |  |  |  |
| controls (saline 10 mg/kg) | — | 40 | — |
| GA | 0.5 | 20 | 27.2 |
|  | 1.0 | 20 | 41.2 |
| $GM_1$ inner ester | 0.5 | 20 | 55.6 |
|  | 1.0 | 20 | 67.1 |
| GA inner ester | 0.5 | 20 | 50.0 |
|  | 1.0 | 20 | 68.2 |

THERAPEUTIC USES

As described in the applicant's above noted patents, the inner ester ganglioside derivatives are useful for the therapy of peripheral nervous system pathologies of traumatic, compressive, degenerative or toxic-infective origins, in which it is necessary to stimulate nervous regeneration and recovery of neuromuscular function and in pathologies of the central nervous system of traumatic, anoxic, degenerative or toxic-infective origin in which it is necessary to stimulate neuronal sprouting to obtain functional recovery.

According to the present invention, it has been found that the inner ester derivatives of gangliosides may be used, due to their precious analgesic properties, as pain relievers in various peripheral neuropathies such as diabetic neuropathies, trigeminal neuralgia, sciatica, cervicobrachial neuralgia, herpes zoster, post-herpetic neuropathies and other neuropathies due to nervous lesions of surgical or compressive origin of a highly painful nature. The inner ester derivatives furthermore may be used for their antiinflammatory (antiexudative) properties. These ganglioside derivatives also have the considerable advantage of being administrable by oral route.

The inner esters of gangliosides according to the present invention may be used as drugs in pharmaceutical preparations destined for administration to man or animal by oral, intramuscular, subcutaneous or intradermal route, by means of pills and injections or intravenous infusions. The preparations intended for oral administration can be in the form of powders or freeze-dried products together with one or more pharmaceutically acceptable excipients made into tablets or capsules. The preparations intended for administration by injection may also be in the form of powders or freeze-dried products with one or more excipients or pharmaceutically acceptable diluents and contained in buffered solutions with a suitable pH and being osmotically compatible with the physiological fluids.

The dosage to be administered depends on the desired effect and on the chosen administration route. For instance, the dosage may be (but not only) between 0.05 and 5 mg of active substance per Kg of body weight/day with a unitary posology of between 0.05 and 2 mg/Kg of body weight. The therapeutic compounds of the present invention are prepared with a mixture of different inner ester derivatives of gangliosides or with only one isolated active derivative.

Table 3 shows a few possible pharmaceutical preparations with analgesic-antiinflammatory properties. The type of pharmaceutical preparation shown in Table 3, used in the case of intramuscular, subcutaneous, intradermal or intravenous administration, is prepared in double flacons. The first flacon (the one containing the active substance) contains between about 10 and 90% w/w of the active substance as a powder or freeze-dried product together with a pharmaceutically acceptable excipient such as glycine or mannitol. The second flacon (with the solvent) contains the desired quantity of solvent, such as sodium chloride and a citrate buffer.

Just before administration, the contents of the two flacons are mixed and the active substance, in the form of a freeze-dried powder, rapidly dissolves giving an injectable solution.

TABLE 3

| Examples of pharmaceutical preparations | | |
|---|---|---|
| System No. 1 | | |
| a. one 2 ml flacon of freeze-dried product contains: | | |
| active substance | mg | 5 |
| glycine | mg | 30 |
| b. one 2 ml vial of solvent contains: | | |
| sodium chloride | mg | 16 |
| citrate buffer in apyrogenic distilled water q.b.a | ml | 2 |
| System No. 2 | | |
| a. one 3 ml flacon of freeze-dried product contains: | | |
| active substance | mg | 5 |
| mannitol | mg | 40 |
| b. one 2 ml vial of solvent contains: | | |
| sodium chloride | mg | 16 |
| citrate buffer in apyrogenic distilled water q.b.a | ml | 2 |
| System No. 3 | | |
| a. one 5 ml flacon of freeze-dried product contains: | | |
| active substance | mg | 100 |

TABLE 3-continued

| Examples of pharmaceutical preparations | | |
|---|---|---|
| mannitol | mg | 40 |
| b. one 4 ml vial of solvent contains: | | |
| sodium chloride | mg | 32 |
| citrate buffer in apyrogenic distilled water q.b.a | ml | 4 |

The type of pharmaceutical preparations shown in Table 4, for use in oral administrations, is represented by examples of tablets and capsules.

Example 1 describes a tablet obtained by direct compression of the components.

Example 3 describes a tablet obtained by granulation in damp conditions and subsequent compression.

Examples 2 and 4 report gastro-resistant tablets.

Example 5 reports a capsule coated in hard gelatin.

Example 6 reports an oil-based capsule.

Example 7 reports a gastro-resistant capsule.

TABLE 4

| Examples of pharmaceutical preparations | | |
|---|---|---|
| Example 1 | | |
| active substance | mg | 100 |
| microcrystalline cellulose | mg | 100 |
| lactose | mg | 20 |
| maize starch | mg | 10 |
| talcum | mg | 5 |
| magnesium stearate | mg | 1.5 |
| Example 2 | | |
| Tablet described in Example 1 with gastro-resistant coating composed of: | | |
| acetophthalate cellulose | mg | 4 |
| hydroxypropylmethylcellulose | mg | 0.2 |
| diethylphthalate | mg | 1.4 |
| shellac | mg | 1.5 |
| Example 3 | | |
| active substance | mg | 20 |
| lactose | mg | 80 |
| maize starch | mg | 50 |
| talcum | mg | 3 |
| magnesium stearate | mg | 1.2 |
| Example 4 | | |
| Tablet described in Example 3 with gastro-resistant coating composed of: | | |
| acetophthalate cellulose | mg | 4 |
| hydroxypropylmethylcellulose | mg | 0.2 |
| diethylphthalate | mg | 1.4 |
| shellac | mg | 1.5 |
| Example 5 | | |
| the granulated product contains: | | |
| active substance | mg | 100 |
| lactose | mg | 80 |
| maize starch | mg | 50 |
| talcum | mg | 3 |
| magnesium stearate | mg | 1.2 |
| Hard gelatin outer coating (Parke-Davis etc.). | | |
| Example 6 | | |
| Oil capsules with the following content: | | |
| active substance | mg | 100 |
| vegetable oil | mg | 320 |
| hydrogenated vegetable oil | mg | 10 |
| bees' wax | mg | 3 |
| soybean lecithin | mg | 5 |
| Hard coating contains: | | |
| gelatin | mg | 120 |
| glycerol | mg | 50 |
| sodium-p-hydroxybenzoate ethyl | mg | 0.6 |
| sodium-p-hydroxybenzoate propyl | mg | 0.3 |
| Example 7 | | |
| Capsule described in Example 5 with hard gastro-resistant coating obtained by a hardening process using formalin solution (according to Scherer's technique) | | |

We claim:

1. A method for treating pain caused by pathologies of the peripheral nervous system comprising administering to a patient in need thereof an effective analgesic and antiinflammatory amount of at least one inner ester ganglioside derivative comprising:
   (a) a saccharide part, at least one ceramide and at least one acid part;
   (b) said saccharide part containing at least one unit of N-acetylgalactosamine or of N-acetylglucosamine and at least one unit of glucose or of galactose;
   (c) said acid unit containing at least one N-acetylneuraminic acid or one N-glycolylneuraminic acid, and
   (d) the carboxy group of at least one of said acid parts being bound by esterification to the hydroxy group of one of said carbohydrates or of one of said acid parts to form a lactonic ring.

2. A method according to claim 1 in which the saccharide part of the ganglioside derivatives has the structure:

where Gal is galactose, GalNAC is N-acetylgalactosamine and Glc is glucose.

3. A method according to claim 1 in which said ganglioside derivatives have at least one N-acetylneuraminic acid bound to at least one of said galactose units.

4. A method according to claim 1 in which at least one of said ganglioside derivatives has the structure:

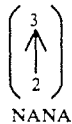
NANA where Gal is galactose, GalNAC is N-acetylgalactosamine, Glc is glucose and NANA is an N-acetylneuraminic acid and where said NANA is bound by esterification to the aforesaid Gal.

5. A method according to claim 1 in which said acid part consists of N-acetylneuraminic acid.

6. A method according to claim 1 in which the saccharide part is composed of units of galactose, glucose and N-acetylgalactosamine.

7. A method according to claim 1 in which the pharmaceutical composition comprises the inner ester of $GM_1$.

8. A method according to claim 7 in which said pharmaceutical composition comprises a mixture of inner esters of $GM_1$, $GD_{1a}$, $GD_{1b}$ and $GT_{1b}$.

9. A method according to claim 8, in which said pharmaceutical composition comprises a mixture of 19–23% by weight of the inner ester of $GM_1$, 36–44% by weight of the inner ester of $GD_{1a}$, 14–18% by weight of the inner ester of $GD_{1b}$ and 17–21% by weight of the inner ester of $GT_{1b}$.

10. A method according to claim 9, in which said pharmaceutical composition comprises a mixture of 40% by weight of the inner ester of $GD_{1a}$, 21% by weight of the inner ester of $GM_1$, 19% by weight of the inner ester of $GT_{1b}$ and 16% by weight of the inner ester of $GD_{1b}$.

11. A method according to claim 1, wherein said composition is administered orally.

12. A method according to claim 8, wherein said composition is administered orally.

13. A method according to claim 9, wherein said composition is administered orally.

14. A method according to claim 10, wherein said composition is administered orally.

15. A method according to claim 7, wherein said composition is administered orally.

16. A method according to claim 1 wherein said composition is administered intradermally.

17. A method according to claim 8, wherein said composition is administered intradermally.

18. A method according to claim 9, wherein said composition is administered intradermally.

19. A method according to claim 10, wherein said composition is administered intradermally.

20. A method according to claim 7, wherein said composition is administered intradermally.